United States Patent [19]

Hartmann et al.

[11] Patent Number: 4,473,696

[45] Date of Patent: Sep. 25, 1984

[54] SYNTHESIS OF 2-SUBSTITUTED-5-METHYL-PYRIDINES

[75] Inventors: Ludwig A. Hartmann, Wilmington, Del.; John F. Stephen, West Chester, Pa.

[73] Assignee: ICI Americas Inc., Wilmington, Del.

[21] Appl. No.: 433,273

[22] Filed: Oct. 7, 1982

[51] Int. Cl.$^3$ .................. C07D 211/70; C07D 223/04
[52] U.S. Cl. .................................................. 546/290
[58] Field of Search .......................... 346/291; 546/290

[56] References Cited

U.S. PATENT DOCUMENTS 3,478,034 11/1969 Campbell et al. ................... 546/250

FOREIGN PATENT DOCUMENTS

| 2718666 | 11/1978 | Fed. Rep. of Germany | 546/291 |
| 726378 | 3/1955 | United Kingdom | 546/250 |
| 955945 | 4/1964 | United Kingdom | 546/243 |
| 967177 | 8/1964 | United Kingdom | 546/243 |
| 1058202 | 2/1967 | United Kingdom | 546/291 |

OTHER PUBLICATIONS

Hubert et al., "Tetrahedron", vol. 31, pp. 1437–1441 (1975).
Moriconi et al., "J. Org. Chem.", vol. 36, No. 19, pp. 2841–2849 (1971).
Brannock et al., "J. Org. Chem.", vol. 26, pp. 625–626 (1961).
Firrell et al., "J. Chem. Soc.", (B) pp. 351–353 (1971).
Mannich et al., "Chem. Ber.", vol. 74, pp. 1629–1643 (1941).
Benzing, "Angew. Chem.", vol. 71, p. 521 (1959).
Brannock et al., "J. Org. Chem.", vol. 29, pp. 801–812 (1964).
Abstract of 140th AOS Meeting (1961), Abstract No. 84, Brannock et al.

*Primary Examiner*—Robert T. Bond
*Attorney, Agent, or Firm*—Louis F. Kreek, Jr.

[57] ABSTRACT

A process for the synthesis of compounds which are known intermediates for the pyridyloxyphenoxy herbicides as well as intermediates used in the process. Propionaldehyde and an acrylic compound, two readily available starting materials, are reacted to form a 2-formylpentanoic compound which is cyclized to a dihydro pyridone which is then oxidized to the 2-hydroxy pyridine. The hydroxypyridine may be halogenated to a 2-halopyridine.

3 Claims, No Drawings

SYNTHESIS OF 2-SUBSTITUTED-5-METHYL-PYRIDINES

BACKGROUND OF THE INVENTION

Various 4-(5-halomethyl-2-pyridyloxy)phenoxy compounds are known to be useful as herbicides as disclosed in European Published patent application No. 483, United Kingdom patent specification Nos. 1,599,121 and 1,599,126 and U.S. Pat. Nos. 4,184,041 and 4,317,913. For example, butyl 2-[4-(5-trifluoromethyl-2-pyridyloxy)phenoxy]propionate which is also known as fluazifopbutyl is an effective grass herbicide which can be used in fields where broad-leaved crops such as cotton and soybeans are cultivated. Important starting materials for such pyridyloxy phenoxy compounds are the 2-halo-5-trichloromethylpyridines such as 2-chloro-5-trichloromethylpyridine described in U.S. Pat. No. 4,317,913. Such 2-halo-5-trichloromethylpyridines, in turn, may be prepared by chlorinating, under ultraviolet light irradiation, a 2-halo-5-methylpyridine as described in U.S. Pat. No. 4,152,328.

An object of the present invention is an efficient, economical and reliable synthesis of 2-halo-5-methylpyridines as well as intermediates used in the synthesis.

A further object of the present invention is a method for preparing 2-halo-5-methylpyridines without utilizing pyridine, and in particular 3-picoline, starting materials to thus avoid the problems of byproduct formation in the halogenation reaction to yield (I) wherein X is halogen.

SUMMARY OF THE INVENTION

The present invention comprises a method for the synthesis of a 5-methylpyridine of the formula (I):

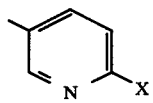

wherein X is a halogen or hydroxy, by condensing the acyclic aliphatic starting materials propionaldehyde and an acrylic ester, amide or nitrile to form a gamma-methyl gamma-aldehydo ester, amide or nitrile which ester may then be aminated with a nitrogen source such as an amine or ammonium compound to form a dihydro-5-methyl-2-pyridone, which amide may be thermally cyclized and which nitrile may be converted to the pyridone via acid catalysis. The pyridone may then be oxidized to the compound of formula (I) wherein X is hydroxy which may be halogenated to the compound of formula (I) wherein X is halo. Also part of the present invention are the individual process steps and novel intermediates formed in the synthesis.

DETAILED DESCRIPTION OF THE INVENTION

In the first step (a) of the process of the present invention, propionaldehyde of the following formula (II) is reacted in a Michael type addition with an acrylic compound of the following formula (III):

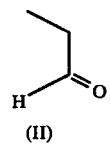 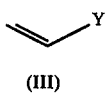

wherein Y is a moiety of the formula —COOR, —CONH₂ or —CN and R is an organic moiety, to produce a pentanoic aldehyde of the following formula (IV):

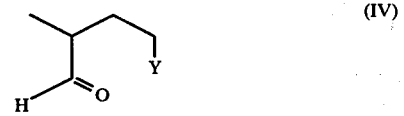

R, in particular, may be a substituted or unsubstituted alkyl or aryl group although a wide range of moieties may be used since the —OR function is removed in the following step. Thus, R may be any grouping which is stable to the Michael addition conditions used and which is removable as the —OR moiety upon nucleophilic attack by a nitrogen on the —COOR group. Particular examples of R are alkyl of about 1 to 6 carbons, e.g., methyl or ethyl, aryl of about 6 to 10 carbons or arylalkyl of about 1 to 8 carbons in the alkyl portion and about 6 to 10 carbons in the aryl portion, which aryl or aryl portion may be substituted by groups such as lower alkyl or halogen. The Michael addition may be conducted as known in the art such as at a temperature of about 0° to 100° C., neat or in the presence of an inert solvent and optionally in the presence of a reaction catalyst such as strong base. The compound of formula (IV) may be recovered by extraction, chromatography or distillation.

Preferably, the first step of the process is conducted in three stages by the use of protection and deprotection reactions which serve to activate the propionaldehye for the Michael addition, to minimize side reactions and to avoid the use of strong reagents and catalysts. The three stages of the first step involve (i) reacting propionaldehye with a secondary amine of the formula HNR¹R², wherein R¹ and R² are independently organic moieties which may be attached to each other to form a ring, to form, directly or through an intermediate aminal the enamine of the following formula (VII):

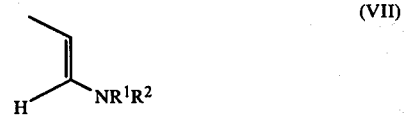

In particular, values of $R^1$ and $R^2$ include individual substituted and unsubstituted alkyl of about 1 to 6 carbons such as ethyl and butyl and, when $R^1$ and $R^2$ are connected, substituted and unsubstituted heterocyclic rings such as 5- or 6-membered heterocyclic rings, e.g., to define the secondary amines pyrrolidine, piperidine and morpholine. The first stage (i) may be conducted at about −10° to 35° C. preferably in the presence of an alkali or alkaline earth metal carbonate, sulfate, halide or oxide, e.g., calcium sulfate, magnesium sulfate, calcium chloride, sodium sulfate, magnesium oxide, potassium carbonate, calcium oxide or even molecular sieves, as disclosed by D. Roelofsen et al. in Recueil, Vol. 91, pages 605-610 (1972), with at least two moles of $HNR^1R^2$ per mole of propionaldehyde. The secondary amine is used in excess in view of the intermediate formation of an aminal of the formula $CH_3CH_2CH(NR^1R^2)_2$ which is then heated to form the enamine of formula (VII) and distil off the excess $HNR^1R^2$ which is released with formation of the double bond. Thus, the aminal may be heated to about 75° to 100° C. at a vacuum of about 40 to 100 mm of Hg. According to this aspect of the present invention, the enamine of formula (VII) and the secondary amine $HNR^1R^2$ are coformed from the aminal and preferably, the $HNR^1R^2$ will be separated from the enamine at this point by fractional distillation. If the secondary amine has a boiling point close to the enamine, e.g., if the secondary amine is morpholine, the distillation should be monitored to avoid codistillation of the two products and/or an incomplete reaction of the aminal. If the aminal is obtained in whole or in part at this point, such may be taken on to the cyclobutane of formula (VIII) as described below. This monitoring can be carried out by gas liquid chromatography and % nitrogen by elemental analysis. Disclosures of such enamine formations include C. Mannich and H. Davidsen in Ber., vol. 69, pages 2106-2112 (1936); G. Opitz et al. in Ann., Vol. 623, pages 112-117 (1959); P. deBenneville et al. in J. American Chemical Society, Vol. 72, pages 3073-3075 (1950); R. Dulou et al. in Bull. Chem. Soc. France, pages 967-971 (1960); G. Kalaus in Ber., Vol. 114, pages 1476-1483 (1981); and E. Benzing U.S. Pat. No. 3,074,940.

In the second stage (ii) of the first step of the invention, the enamine of formula (VII) is reacted with the acrylic compound of formula (III) to yield the compound of the following formula (VIII):

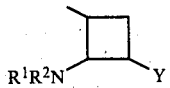

(VIII)

wherein Y, $R^1$ and $R^2$ are as defined above for formulae (III) and (VII). The compound of formula (VIII) may exist to a limited extent in the form of the open chain enamine of the structure $(R^1R^2N)HC=CHCH_3(CH_2)_2Y$. The synthesis of cyclobutanes of the formula (VIII) type is described in detail by I. Fleming et al. in the Journals of the Chemical Society, pages 2165-2174 (1964) and in U.S. Pat. Nos. 3,051,622; 3,133,924; 3,369,024; 3,481,936; and 3,481,939. The reaction may be carried out neat or in the presence of a nitrile, ether, ester, halogenated alkane or ketone solvent, e.g., acetonitrile, although a neat reaction is preferred in view of simplicity. The reaction may be carried out at room temperature up to the boiling point of the acrylic compound of formula (III), e.g., up to about 170° C., with the higher temperatures of this range being advantageously used to complete the reaction. The enamine of formula (VII) may be cooled to about −5° to 20° C. with dropwise addition of the acrylic compound of formula (III) followed by warming to the range of room temperature to about the boiling point of the acrylic compound.

The third stage (iii) of the first step of the invention process is the hydrolysis of the compound of formula (VIII) to the aldehyde of formula (IV) with recovery of one mole of the secondary amine $HNR^1R^2$. The reaction may be conducted in an aqueous acidic medium such as in the presence of an aqueous organic or mineral acid, such as acetic, sulfuric, hydrochloric, phosphoric or toluene sulfonic acids, optionally with a solvent such as those listed for the second stage (ii) of the first step, at a temperature of about 25° to 105° C. at a pH of about 1.5 to 4.5. The solvent for this reaction may advantageously be that used in stage (ii) whereby the product of stage (ii) need not be purified but rather may be simply carried forward in its crude state with solvent. However, a solvent other than the aqueous acidic reaction medium need not be present. The aldehyde of formula (IV) may be recovered by extraction of the aqueous acid solution containing $HNR^1R^2$ with a neutral organic solvent such as ethyl acetate or methylene chloride. Alternatively, the third stage hydrolysis (iii) may be conducted under basic conditions and in the event of saponification of the ester, the acid is formed, i.e., the compound of formula (IV) wherein Y is —COOR and R is hydrogen, and such may be cyclized to the dihydropyridone of formula (V) as explained below. A disclosure of reactions leading to (IV) wherein Y is —COOCH_3 was made by W. Pirkle et al. in the Journal of Organic Chemistry, Vol. 40, pages 1617-1620 (1975) with similar reactions being described by G. Stork in the Journal of the American Chemical Society, Vol. 85, pages 207-221 (1963). The reaction of acrylonitrile, i.e., compound (III) where Y=CN, with the pyrrolidine enamine of n-heptaldehyde is described by Ross C. Terrell, Ph.D. Thesis Columbia University (1955) as yielding α-cyanoethyl-n-heptaldehyde and compound (IV) where Y=CN may be produced in a similar manner.

In the second step (b) of the process of the invention when Y=COOR, the aldehyde of formula (IV) is reacted with an amine or ammonium salt to form the dihydropyridone of the following formula (V):

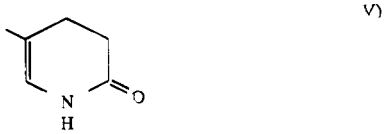

(V)

The cyclization in step (b) may be carried out with a nitrogen source such as an amine or ammonium salt, with specific examples being ammonium carbamate, ammonium carbonate, ammonium hydroxide, ammonia, ammonium bicarbonate, ammonium acetate or ammonium orthophosphate. In general, an ammonium salt of a weak acid such as phosphoric, carbonic or acetic acid is preferred. The reaction may be carried out neat or in a solvent, e.g., a high boiling solvent, for one or both reactants such as a carboxylic acid, e.g., acetic acid, an alkanol which use is less preferred, e.g., ethanol, an aromatic hydrocarbon compound, e.g., benzene or toluene, a halogenated aromatic hydrocarbon, e.g., a mono-, di- or tri-chlorobenzene, or a ketone, e.g., methyl ethyl ketone, methyl isobutyl ketone and disobutyl ketone. The temperature of the cyclization reaction will vary depending on the particular nitrogen source used and the solvent but is, in general, from about room temperature up to the boiling point of any solvent or reactant utilized, e.g., from about 25° to 150° C.

In the second step (b) of the process of the invention when Y=CONH_2 the aldehyde of Formula (IV) is thermally cyclized at a temperature of about 100° to 200° C. neat or in a high boiling solvent such as aromatic hydrocarbon compound, e.g., benzene, xylene or acrylamide, or a halogenated aromatic hydrocarbon, e.g., a mono-, di- or tri-chlorobenzene and the pyridone of formula (V) may be recovered by standard techniques such as distillation or extraction.

In the second step (b) when Y=CN, the aldehyde (IV) is converted to the pyridone (V) by acid catalysis, e.g., with hydrogen halide such as HCl, sulfuric acid, phosphoric acid or a sulfonic acid at a temperature of room temperature to about 100° C. neat or in a solvent such as a halogenated hydrocarbon. Such reaction conditions are described by N. P. Susherina et al. in Chemical Abstracts, Vol. 55 7410e, by A. I. Meyers in J. Organic Chemistry, Vol. 29, pages 1435-1438 (1964) and in German Offenlegundschrift No. 2,245,097 (Mar. 21, 1974).

In one aspect of the invention, the cyclization step (b) may be conducted in two stages by (iv) dimerizing the aldehyde of formula (IV) where Y=COOR by reaction with excess ammonia or other nitrogen source to yield the pyridone adduct of the following formula (X):

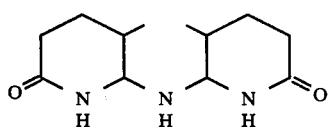

(X)

followed by (v) pyrolyzing the compound of formula (X) with loss of NH$_3$ at a temperature of about 200° to 300° C. to yield the dihydropyridine of the formula (V).

In the third step (c) of the process of the present invention, the dihydropyridone of formula (V) is oxidized to the pyridone of the following formula (VI):

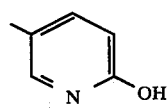

(VI)

In one aspect of the present invention, the oxidation step (c) may be carried out by a first stage (vi) comprising dihalogenating the compound of formula (V) with a halogenating agent such as chlorine, bromine, sulfuryl bromide or sulfuryl chloride in an equimolar to slight molar excess at about 25° to 40° C. in a solvent such as a halogenated hydrocarbon, e.g., chloroform or chlorobenzene, to produce the dihalo compound of the following formula (IX):

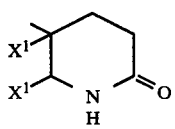

(IX)

wherein $X^1$ is a halogen atom, such as chloro or bromo. In a further stage (vii), the dihalo compound of formula (IX) may then be dehydrohalogenated to produce the pyridine of formula (VI) by heating to a temperature of about 100° to 170° C. neat or in the presence of a high boiling solvent such as chlorobenzene. In general, the product of the dehydrohalogenation stage (vii) is the hydrohalide salt of the pyridine of formula (VI) which may be carried on directly to the 5-methylpyridine of formula (I) wherein X is a halogen, or may be first converted to the free base by neutralization in an aqueous base such as sodium hydroxide or sodium carbonate followed by vacuum evaporation and extraction with an organic solvent such as hot acetone or ethanol. The halogenation of various dihydro pyridones is described by N. P. Shusherina et al. in Chemical Abstracts, Vol. 55 7410f (1961), Vol. 60 4101 (1964), vol. 58 9011d and 12507h (1963) and by D. Diller et al. in Berichte Vol. 110, pages 2956-2957 (1977).

In the dihalogenation stage (vi) used to produce the dihalo compound of formula (IX), several products have been observed which may be readily converted to pyridone of formula (VI) together with or separate from the dihalo compound (IX). In particular, the reaction conditions described above for stage (vi) have yielded both the hydroxy halo compound of the following formula (XI) when water is present:

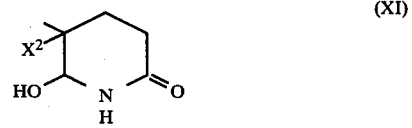

(XI)

wherein $X^2$ is a halogen such as bromo or chloro, and the dimeric compound of the following formula (XII):

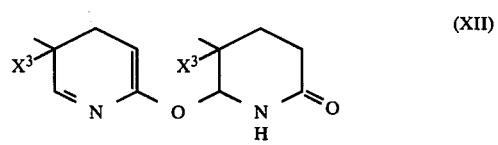

(XII)

wherein $X^3$ is a halogen such as bromo or chloro. In general, use of lower temperatures for the dihalogenation stage (vi) will produce compound (IX) while higher temperatures, e.g., about 40° to 80° C. will yield the by-products (XI) and/or (XII). Thus, at a reaction temperature of 40° to 80° C. for 2 hours in toluene with a 50% molar excess of sulfuryl chloride, compound (V) may be vacuum evaporated and extracted with toluene to leave insolubles which include the compound of formula (XI) wherein $X^2$ is chloro, m.p. 135° to 142° C. If the same reaction is conducted in chloroform at 30° to 60° C., the crystaline product contains the dimer of formula (XII) wherein $X^3$ is chloro, m.p. 157° to 159° C. The hydroxy halo compound (XI) and dimeric compound (XII) may be converted to the pyridine (VI) by heating to about 175° to 250° C. neat or in the presence of a high boiling solvent. An advantage of the invention process that the by-products of this step can be converted to the next stage product in the same manner as the desired product, i.e., (XI) and (XII) are converted to (VI) in the same manner as (IX) would be.

The oxidation step (c) may also be carried out by reacting the dihydropyridone of formula (V) with a halogenating agent such as N-chloro- or N-bromo-succinimide or 1,3-dichloro- or 1,3-dibromo-5,5-dimethylhydantoin which adds halogen at an allylic position or the position alpha to the carbonyl, i.e., the 3- or 4-halo-2-pyridone to yield the compound of the following formula (XIII):

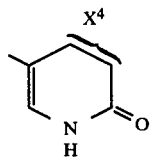

wherein X[4] is halogen such as bromo or chloro. The compound of formula (XIII) may then be converted to the pyridine of formula (VI) by thermal elimination of HX[4].

In the final step (d) of the overall process of the invention, the pyridone (VI) is halogenated with a halogenating agent such as a sulfur halide, e.g., thionyl chloride, sulfuryl chloride, a carboxylic acid halide, e.g., phosgene, or a phosphorus halide such as phenylphosphonic dichloride, phosphorus oxychloride or phosphorus pentachloride, in a high boiling solvent such as a aromatic hydrocarbon solvent, e.g., toluene or xylene, or a halogenated aromatic hydrocarbon, e.g., chlorobenzene, at a temperature of about 90° to 120° C. to yield the compound of formula (I) wherein X is a halogen, e.g., chloro bromo or iodo. The molar ratio of halogenating agent:compound of formula (VI) may vary, e.g., a ratio of $POCl_3$: (VI) of about 1.5:1 to 4.5:1 or of $PCl_5$: (VI) of about 0.3:1 to 0.5:1 may be used. In addition, a combination of phosphorus halides may be used, e.g., a mixture of $POCl_3$ and $PCl_5$ in a molar ratio of 1:0.1 or 1.6:0.45. Thus, the molar ratio of halide atoms in the phosphorous halide:compound of formula (VI) should be about 6:1. The reaction of 2-hydroxy-5-methylpyridine to yield 2-chloro-5-methylpyridine is also described by W. Herz et al. in the Journal of Organic Chemistry, Vol. 22, pages 122–125 (1961).

Particular aspects of the process of the present invention which are advantageous are high yields obtained, the novel skeletal formation of a β-picoline while simultaneously functionalizing the 2-position with a group which is readily transformed to chlorine and the in situ generation of the ammonium compound such as ammonium acetate in the conversion of the compound of formula (IV) to (V).

Also part of the present invention are novel intermediates as described herein.

In the following Examples and throughout the specification, the following abbreviations are used: °C. (degrees Centigrade); ml (milliliters); g (grams); m (moles); mm (millimeters); GLC (gas liquid chromatography); GC/MS (gas chromatograph-mass spectrometry); IR (infrared); NMR (nuclear magnetic resonance); mp (melting point); bp (boiling point); d$_6$-DMSO (deuterated dimethyl sulfoxide); and the conventional symbols for the chemical elements.

EXAMPLE 1

Step (a), stage (i) to yield morpholinopropene of formula (VII) ($NR^1R^2$=morpholine)

A 500 ml 4-neck flask was equipped with a stirrer, thermometer, addition funnel and condenser. To the flask was charged 191.7 g (2.2 m) of morpholine and 138.2 g (1 m) of potassium carbonate (anhydrous) and the mixture was stirred and cooled to −5° C. with an ice-salt bath. To the flask was added 58 g (1 m) of propionaldehyde over a period of 55 minutes at a pot temperature of −5° C. The temperature was then allowed to rise to 25° to 27° C. and the reaction was continued for 2 hours at 25° C. The product was filtered and the filter cake washed with four 15 ml washes of toluene. The fitrate was heated under vacuum while morpholine was stripped using a 1 foot Vigreux column. This treatment was carried out at an oil bath temperature of 85° to 112° C., a pot temperature of 70° to 90° C., a vapor temperature of 41° to 58° C. and at a pressure of approximately 35 to 40 mm of Hg. The vacuum stripping was carried out until 133.3 g of product was obtained as a residue. GLC and GC/MS established that the predominant product was 4-(2-propenyl)morpholine.

$^{13}$C NMR in d$_6$—DMSO (in δ units):15.2 (CH$_3$) 95.1 (CH$_3$—CH)=; 140.8 (—CH=CH—); 49.4 (—N(—CH$_2$—)$_2$); and 66.1 (O(—CH$_2$—)$_2$).

EXAMPLE 2

To a thin slurry of 191.7 g (2.2 m) of morpholine and 84.0 g (1.5 m) of calcium oxide was added dropwise 58 g (1 m) of propionaldehyde over a 30 minute period at 15° C. The reaction was mildly exothermic and some cooling was applied. The slurry was filtered after 30 minutes reaction time at 25° C. and the filter cake was washed with two 40 ml washes of morpholine. The filtrate was gradually heated to 75° to 85° C. under vacuum and then held at 85° C. pot temperature and a pressure of 40 mm of Hg vacuum over 2 hours while distilling morpholine in a Vigreux column. The product pot residue weighed 116.6 g.

EXAMPLE 3

Step (a), stage (ii) to yield acrylic compound of formula (VIII) (Y=COOR; R=CH$_3$; $NR^1R^2$=morpholine)

A solution of 40 g of crude morpholinopropene produced in Example 1 in 175 ml of acetonitrile is cooled to −2° C. in an ice-salt bath and treated with a solution of 30.5 g (0.35 m) of methylacrylate in 70 ml of acetonitrile dropwise over a period of 20 minutes at −2° to 0° C. The temperature of the solution is then gradually raised and held at 66° to 76° C. for 17 hours. At that point, a predominate product peak can be detected by GLC together with a smaller unidentified peak while at the same time, the morpholinopropene peak has almost completely disappeared. The methyl 3-methyl-2-(4-morpholinyl)cyclobutane carboxylate was characterized by GC/MS and NMR.

$^{13}$C NMR in d$_6$—DMSO (in δ units):66.3 (O(—CH$_2$—)$_2$); 50.2 (—N(—CH$_2$—); 70.8 (N—CH); 31.0 (CH$_3$—CH); 26.2 (cyclobutane—CH$_2$—); 39.1 (CH—COOCH$_3$) 174.1 (—COOCH$_3$); 51.4 (—COOCH$_3$); and 20.6 (CH—CH$_3$).

EXAMPLE 4

To 63.5 g of the crude morpholinopropene product of Example 2 was gradually added 45.7 ml (0.51 m) of methyl acrylate at room temperature. The reaction mixture was then heated to 80° C. until the reaction was complete in 7 hours as determined by GLC. The yield of product was 106.4 g with no loss during vacuum stripping to remove unreacted acrylate at 1 hour at 55° C. under a pressure of 50 mm of Hg.

EXAMPLE 5

Step (a), stage (iii) to yield methyl 4-formylpentanoate of formula (IV) (Y=COOR; R=CH$_3$)

A solution of 18 g (0.3 m) of acetic acid in 120 ml of water is added to the crude morpholino cyclobutane carboxylate ester product of Example 3 and the reaction mixture is heated at 70° to 79° C. for 5 hours. The product solution is cooled to room temperature, diluted with 150 ml of water and extracted 3 times with ethyl acetate, 100 ml each wash. The extracts were washed 2 times with dilute sodium chloride brine solution and methyl 4-formylpentanoate is obtained after vacuum stripping at 60° to 70° C. and a moderate vacuum of 100 mm to 28 mm of Hg in a yield of 29.2 g.

The crude methyl 4-formylpentanoate obtained above was purified by distillation at 83° to 85° C. at 6 mm to 8 mm of Hg with 90% recovery. Purity by GLC after distillation was determined to be 95.3% and the product was characterized by IR, NMR and GC/MS.

$^{13}C$ NMR in $d_6$—DMSO (in δ units):51.4 (—COOCH$_3$); 173.2 (—COOCH$_3$); 31.0 (—CH$_2$—COOCH$_3$); 25.4 (—CH$_2$—CH$_2$—COOCH$_3$); 45.1 (CH—CH$_3$); 13.0 (CH—CH$_3$); and 204.7 (—CHO).

EXAMPLE 6

To a sample of 53.2 g (0.19 m) of undistilled morpholino cyclobutane ester prepared as in Example 4 was added with stirring at 26° C. 46.3 ml (0.19 equivalents) of 4.1 Normal H$_2$SO$_4$. The temperature rose to 42° C. and the reaction mixture was then heated to 98° C. and held under reflux for 3.5 hours to produce a two-phase reaction product. The upper layer was separated, diluted with 25 ml of methylene chloride and extracted twice with water, 25 ml each. Vacuum evaporation of the methylene chloride yielded 25.6 g of methyl 4-formyl pentanoate which was 87.5% pure by GLC.

EXAMPLE 7

To a sample of 103.6 g (0.41 m) of morpholino cyclobutane carboxylate ester prepared as in Example 4 was slowly added with stirring an aqueous HCl solution made up of 41 ml of concentrated HCl mixed with 48 ml of water to result in 0.49 m of HCl. During the addition over 0.75 hours, the temperature rose to 70° C. and the reaction mixture was then heated to 106° C. under reflux for 3½ hours to yield a two phase reaction product. The upper layer was separated in a separatory funnel and the lower aqueous layer was extracted three times with methylene chloride, 70 ml each. The combined extracts were washed once with 80 ml of water, vacuum evaporated and combined with the upper product layer yielding 49.1 g of methyl 4-formylpentanoate which was 97% pure by GLC.

EXAMPLE 8

Step (b) to yield 5-methyl-3,4-dihydro-2(1H)pyridone of formula (V)

To 1.44 g (0.01 m) of methyl 4-formylpentanoate dissolved in 10 ml of acetic acid was added 1.54 g (0.02 m) of ammonium acetate and the mixture was heated at 80° to 125° C. for 16 hours. GLC showed about 11% unreacted starting material, 89% of the desired title product and no by-products. The product was vacuum stripped, dissolved in 10 ml of ethyl acetate and washed 4 times with water, 2.5 ml each wash. The product was distilled after vacuum stripping of ethyl acetate to yield 0.5 g of 5-methyl-3,4-dihydro-2(1H)pyridone, bp 103° C. at 0.5 mm of Hg. The product was recrystallized from ethyl acetate, mp, 76° to 78° C.

Elemental Analysis: N, 12.13% (Calculated 12.8%).

$^{13}C$ NMR in $d_6$—DMSO (in δ units):19.0 (CH$_3$); 169.0 (C=O); 30.1 (CH$_2$ α to C=O); 25.5 (CH$_2$ β to C=O); 112.0 (C(CH$_3$)=CH); and 120.3 (CH directly attached to NH)

EXAMPLE 9

The procedure of Example 8 was repeated utilizing 33.7 g (0.234 m) of methyl 4-formylpentanoate, 36 g (0.467 m) of ammonium acetate and 200 ml of acetic acid at 105° C. with a reaction time of 22 hours. The product was vacuum stripped at 65° to 95° C. bath temperature at 10 mm of Hg and 200 ml of distillate were collected. The residue was dissolved in 200 ml of toluene and washed four times with 50 ml of water each time. The aqueous extracts were washed two times with 70 ml of toluene each time and the combined toluene extracts were vacuum stripped at 40° to 50° C. at 80 to 100 mm of Hg. The yield of 5-methyl-3,4-dihydro-2(1H)-pyridone which solidified at room temperature was 13.6 g (52% yield).

EXAMPLE 10

A neat reaction was conducted to yield 5-methyl-3,4-dihydro-2(1H)pyridone by mixing 10 g (0.0693 m) of 4-formylpentanoate and 10.7 g (0.139 m) of ammonium acetate at room temperature followed by stirring and heating to 100° to 110° C. for 1.5 hours. A fairly vigorous reaction occurred at 95° C. with bubbling and release of some NH$_3$. After four washings of the residue with 10 to 15 ml of chlorobenzene, the product was shown in the chlorobenzene to have a yield of 73% by GLC.

EXAMPLE 11

A sample of 5 g (0.0347 m) of 4-formylpentanoate was stirred with 3.57 g (0.045 m) of ammonium bicarbonate and heated to 40° C. To the mixture was gradually added 3 g (0.05 m) of acetic acid at 41° to 45° C. over 35 minutes while the initial foaming disappeared. The clear solution was heated at 92° to 97° C. for 2 hours to yield 9.28 g which was distilled at a bath temperature of 100° to 122° C. at about 1 mm of Hg vacuum to yield 2.14 g of the compound of formula (V) which was 98.5% pure by GLC analysis.

EXAMPLE 12

To 5.4 g of 4-formylpentanoate was added 5.6 g (a 95% excess) of ammonium acetate and 50 ml of ethanol. The reaction was carried out at 30° C. for 5 hours and the ethanol was then vacuum stripped after 16 hours at room temperature. The product was partitioned in 30 ml toluene and 10 ml of water, the water layer was discarded and the toluene layer was refluxed at 82° to 88° C. for 3 hours. The product was obtained by vacuum evaporation of the toluene and the purity of the 5-methyl-3,4-dihydro-2(1H)-pyridone was 81% by GLC.

During this reaction, a reaction intermediate, probably the methyl 4-iminopentanoate, was detected by GLC when the reaction was carried out for only 10 minutes to 1 hour.

EXAMPLE 13

To 6.0 g (0.0416 m) of methyl 4-formylpentanoate in 15 ml of absolute ethanol is added 10.5 g of a NH$_4$OH solution (prepared from 33.3 g of a 30% NH$_4$OH solution and 100 ml of water). The reaction was carried out at room temperature for 20 hours followed by vacuum stripping at 30° to 55° C. under a moderate vacuum of about 200 to 40 mm of Hg. Distillation of the product under forcing conditions of a pot temperature of 125° to 130° C. at a pressure of 1 mm of Hg gave a fraction distilling at 100° to 110° C. which was identified as 5-methyl-3,4-dihydro-2(1H)pyridone. The product was 95.3% pure by GLC.

EXAMPLE 14

A solution of 5 g of methyl 4-formylpentanoate in 15 ml of chlorobenzene was slowly added to a solution of 3.0 g of ammonium acetate in 15 ml of chlorobenzene which is then held at 90° to 100° C. The volatiles were allowed to distill during the reaction so that the temperature could be maintained at 98° C. for 1.5 hours after the addition. Gradually, clearing took place during the 1.5 hours and GLC of the product showed only 5-methyl-3,4-dihydro-2(1H)pyridone and a small amount of starting material. Distillation yielded the desired products as a white crystaline solid in 90% yield.

The above reaction was repeated using 3.1 g of ammonium bicarbonate and 2.6 g of acetic acid in the place of the ammonium acetate.

EXAMPLE 15

To a reaction vessel was charged 380 ml of chlorobenzene followed by 67 g (1.11 m) of glacial acetic acid. To the vessel was then added 63.5 g (1.12 m) of ammonium hydroxide in the form of a concentrated aqueous solution over 5 minutes at 25° to 37° C. while stirring and cooling with an ice bath. The temperature was then raised to 90° C. at which point the addition of a solution of 127 g (0.88 m) of methyl 4-formylpentanoate in 254 ml of chlorobenzene was started. The methyl 4-formylpentanoate was added over 40 minutes while the temperature was held at 90° to 96° C. The reaction mixture was two-phased and was continuously heated at 90° to 95° C. while volatiles were allowed to distill off. One hour after complete addition, GLC analysis showed little unreacted pentanoate and after two hours, only about 2% was unreacted. The product was isolated by vacuum stripping of chlorobenzene at a pot temperature of 60° to 85° C. with a final vacuum of 20 mm of Hg. The product of formula (V) was then distilled at a pot temperature of 100° to 150° C., a vapor temperature of 93° to 113° C. at about 1 mm of Hg. The yield of formula (V) as a yellow solid was 83.6 g (0.75 m) which was 99% pure by GLC (85% yield).

EXAMPLE 16

Steps (a) and (b) to yield
5-methyl-3,4-dihydro-2(1H)-pyridone of formula (V)
via acrylamide of formula (III) (Y=CONH$_2$)

A sample of 25 g of morpholinopropene of the formula (VII) was dissolved in 80 ml of acetonitrile at room temperature and treated with a warm solution of 39.1 g of acrylamide in 100 ml of acetonitrile dropwise at a reaction temperature of 25° C. The temperature was then raised to 80° to 85° C. and held there for about 40 hours. The product was filtered hot to remove a small amount of insoluble matter and was then treated with a solution of 12 g of glacial acetic acid in 80 ml of water at 75° to 80° C. for 6.5 hours. The product was vacuum-stripped at 48° C. under moderate vacuum to remove acetonitrile and the residue was washed with toluene and ethyl acetate. GLC of the aqueous solution showed a composition of about 2:1 acrylamide:aldehyde of formula (IV) (Y=CONH$_2$). The aqueous solution was vacuum-stripped at 50° to 60° C. under 40 mm of Hg pressure to leave the product as a light amber viscous residue. This was treated with 100 ml of ethanol, crystallized and filtered to remove part of the acrylamide. Final vacuum-stripping gave 58.9 g of residue consisting of acrylamide and 4-formylpentanamide. The product of formula (V) was generated thermally from this product by treatement at 100° to 140° C. under high vacuum. During this treatment, 12.5 g of distillate was produced comprising the compound of formula (V) and acrylamide. Remaining was 35 g comprising compound (V) and morpholinopropionamide. GLC analysis showed that the distillate contained about 40% by weight (V) while the residue contained 20% (V). Addition of acetonitrile to the distillate and hot ethyl acetate to the residue gave acrylamide as a crystalline solid, mp 76° to 80° C. from the distillate and morpholinopropionamide, mp 94° to 100° C. as a crystalline solid from the residue. The compound of formula (V) was found in the solutions after crystallizations to the extent of about 60%.

EXAMPLE 17

Step (b), stages (iv) and (v) to yield the pyridone adduct
of formula (X) as an intermediate and
5-methyl-3,4-dihydro-2(1H)pyridone of formula (V) as
a final product.

To 2.0 g of methyl 4-formylpentanoate was added with stirring 9 ml of concentrated ammonium hydroxide solution gradually and an exothermic reaction took place with a temperature rise from 25° to 55° C. After ½ hour, GLC showed 99% product and the temperature was then held at 88° to 96° C. for 1 additional hour and the product was then vacuum stripped at 80° C. under a pressure of 5 to 20 mm of Hg for ½ hour. Although the GLC analysis showed product with a very high purity, the NMR analysis determined that no 5-methyl-3,4-dihydro-2(1H)pyridone was present. The conclusion reached is that an intermediate was prepared which converted to the desired product under GLC injection conditions. Isolation of the intermediate was carried out by crystallization with 3 ml of ethyl acetate. The yield of several fractions was 25% as a crystaline white solid, mp, 158° to 166° C. The compound was insoluble in ethanol, acetone and toluene but soluble in methylene chloride. The product was dissolved in a hot mixture of 7 parts by volume of methanol and 9 parts by volume of ethyl acetate and recrystallized to give an mp of 182° to 184° C.

Elemental Analysis: N, 17.0% (Calculated for the compound of formula (X) as $C_{12}H_{21}N_3O_2$, N, 17.55%).

$^{13}C$ NMR in CDCL$_3$ (shift of −77.0 ppm using CDCL$_3$ as the standard) (in δ units):174.6, 173.4 (C=O); 31.3, 30.6 (CH$_2$—C=O); 26.3, 23.3 (CH$_2$—CH$_2$—C=O); 35.8, 33.3 (CH—CH$_3$); 75.3, 71.0 (NH—CH—NH): and 17.9, 17.7 (CH$_3$).

EXAMPLE 18

The high-melting intermediate prepared in Example 17 was prepared under milder conditions by treating 2 g (0.014 m) of 4-formylpentanoate in 5 ml of absolute ethanol with 3.5 g (0.02 m) of dilute NH$_4$OH solution (prepared from 33.3 g of a 30% NH$_4$OH solution and 100 ml of water) at room temperature. GLC samples taken during the reaction showed a mixture of starting material, the desired product peak due to the intermediate of formula (X) and methyl 4-iminomethylpentanonate. After 24 hours at room temperature, the major peak was the product. The reaction mixture was vacuum evaporated at 60° C. under 1 to 6 mm of Hg to give 1.5 g of product which was recrystallized from 3.5 ml of ethyl acetate, mp 171° to 174° C.

The product of formula (X) was recrystallized from excess acetone/methanol to yield crystals, mp 178° to 182° C.

Elemental Analysis: C, 59.85% (Calculated 60.2%); H, 8.63% (Calculated 8.85%): N, 17.58% (Calculated 17.55%).

EXAMPLE 19

Step (c), stages (vi) and (vii) to yield the dihalo compound (IX) ($X^1$=Cl) as an intermediate and pyridone (VI) as a final product.

A solution of 1.5 g (0.0135 m) of 5-methyl-3,4-dihydro-2(1H)pyridone of formula (V) in 9 ml of chloroform was treated with sulfuryl chloride dropwise at 25° to 33° C. After 1 hour at 30° C., a GLC in ethanol solution (with potassium hydroxide) showed conversion of the starting material to the chloro ethoxy adduct indicating reaction of chlorine across the double bond with no starting material. After 2 hours at 33° C., the product was vacuum stripped at 15° to 45° C. over a period of 3 hours gradually reducing the pressure from 200 to 15 to 30 mm of Hg. The yield was 2.63 g of a colorless amorphous product of the formula (IX) wherein $X^1$ is chloro. A sample of 2.32 g of this product was stirred with magnet for 1.5 hours at a bath temperature of 132° to 138° C. under 12 to 35 mm of Hg. The yield was 1.57 g of product of the formula (VI) as the hydrochloride and free base.

The free base of the compound of formula (VI) was generated by adding 4 ml of water followed by 0.4 g of sodium carbonate to the product produced in the above paragraph to result in a pH of 9 and vacuum stripping followed with recovery of the pyridone of formula (VI) by washing the residue with warm acetone to yield 0.53 g of the compound of formula (VI) in the acetone, mp, 150° to 172° C. Preferably, the extraction with warm acetone is replaced by an ethanol extraction.

In a similar example, the product was recrystallized from methanol to yield a product with a melting point of 178° to 180° C.

EXAMPLE 20

The procedure of Example 19 was repeated utilizing 5 g of the starting material of formula (V). The free base was generated with 15 ml of water and 1.7 g of sodium carbonate at a pH of 8.5 and the mixture was then vacuum stripped to remove water. The residue was washed with hot ethanol and the ethanol was then vacuum stripped to yield the product of formula (VI), mp 119° to 147° C.

EXAMPLE 21

The procedure of Example 19 was repeated with the substitution of chlorobenzene, also known as monochlorobenzene, for chloroform as follows. The reaction was carried out using 4 g of the product of formula (V), 8 ml of chlorobenzene and 4.4 ml of sulfuryl chloride of the formula $SO_2CL_2$ (a 50% excess). The dropwise addition of sulfuryl chloride was carried out at 23° to 38° C. with slight cooling followed after one hour by application of a vacuum of 75 to 150 mm of Hg at 27° to 38° C. for 1 hour. The temperature is then raised to 129° C. in the pot and 141° to 143° C. in the oil bath at a pressure not less than 220 mm of Hg for 3 hours. The product precipitates out as a fairly fluid lower layer during the reaction, is quite viscous on cooling and consists of the compound of formula (VI), partly in the form of the hydrochloride salt.

EXAMPLE 22

Into a solution of 7.0 g of the compound of formula (V) in 35 ml of chlorobenzene at 20° C. was introduced 7 g of chlorine gas over a period of 30 minutes. This solution was added gradually over 1 hour to 15 ml of chlorobenzene at 130° C. while nitrogen was bubbled through the solution. After addition, the reaction was continued for 4 hours as the product precipitated. To the product was added 18 ml of water and the product mixture was neutralized to a pH of 8.5 in the aqueous phase with 5 ml of 5 Normal NaOH. After vacuum stripping, the product was dissolved with ethanol and diluted to a volume of 100 ml. This solution was analyzed by GLC and found to contain 5.4 g of the compound of formula (VI) (78.6% yield).

EXAMPLE 23

Steps (c) and (d) to yield compound (I) (X=Cl) without isolation of pyridine (VI)

A sample of 4 g of crystallized 5-methyl-3,4-dihydro-2(1H)pyridone of formula (V) was dissolved in 8 ml of chlorobenzene and was treated with 4.4 ml of sulfuryl chloride as described in Example 20. After dehydrohalogenation at 129° C., the product consisted of a lower dark product phase which was very viscous at 40° C. To the slurry of both phases was added 10.4 ml of $POCl_3$ at 40° over ½ hour followed by 3.4 g of phosphorous pentachloride. The mole ratio of the product of formula (VI):$POCl_3$:$PCl_5$ was 1:3:0.45. The reaction mixture became homogenous and was heated at 116° to 118° C. for 4 hours. To the product was then added to 50 g of crushed ice, 50 ml of chlorobenzene and 162 ml of a 13% aqueous sodium hydroxide solution. Phase separation was made in a separatory funnel and the lower aqeuous layer was extracted 3 times with 20 ml of chlorobenzene each. The product layer and chlorobenzene extracts were combined and analyzed by GLC. The thus-produced chlorobenzene solution contained 1.5 g of the product of formula (I) wherein X is chloro.

EXAMPLE 24

Into a solution of 7.0 g of the compound of formula (V) in 35 ml of chlorobenzene was introduced 8.0 g of chlorine gas at 20° over a period of 1.25 hours. This solution was added gradually to 15 ml of stirred chlorobenzene held at 130° C. over a period of 1 hour. The reaction was continued at 130° C. for 4.5 hours and the product slurry was cooled to 60° C. To this was then added 14.5 g of $POCl_3$ dropwise over 15 minutes followed by 2.62 g of $PCl_5$ also at 60° C. The reaction mixture was heated to 115° C. for 4.5 hours. For the purposes of analysis, the product was added to 40 ml of methanol, vacuum stripped at 50° C. at 130 mm of Hg and the addition of methanol and vacuum stripping was repeated. The product was then neutralized to a pH of 6 with 45 ml of alcholic KOH solution, prepared from 16 g of KOH in 100 ml of methanol, and diluted to 100 ml with methanol. The product solution was analyzed by GLC and was found to contain 4.85 g of the compound of formula (I) wherein X is chloro.

EXAMPLE 25

Step (d) to yield compound (I) (X=Cl)

To 4.2 g of the compound of formula (VI) was added 15 ml of POCl$_3$ at 25° to 34° followed by 3 g of PCl$_5$. The reaction mixture was stirred and heated at 110° C. for 4 hours and gradual solution took place. The product was added to 100 g of crushed ice and neutralized to pH 8 with 80 ml of 15% sodium hydroxide while cooling. The aqueous solution was extracted 5 times with 24 ml of methylene chloride each. The extracts were analyzed by GLC and evaporated at 40° C. at 4 mm of Hg to a constant weight. The yield was 3.9 g of the compound of formula (I) wherein X is chloro.

Elemental Analysis: Cl, 26.55% (Calculated, 27.8%); N, 10.75% (Calculated, 10.98%).

The GLC retention times and NMR of the product were identical to those of authentic samples of the compound of formula (I) wherein X is chloro.

EXAMPLE 26

In the above Example 25, separations of the product phase from the aqueous phase may be difficult and incomplete if the product phase is too concentrated. A more dilute system is believed to be more practical as described below.

The procedure of Example 25 was repeated with a 1:1 (w:w) dilution (weight:weight of the compound of formula (VI) with chlorobenzene. A sample of 3.0 g of compound (VI) was mixed with 3 g of chlorobenzene and 4 ml of POCl$_3$ were added gradually at 25° to 32° C., followed by 2.6 g of PCl$_5$ at 27° to 32° C. The slurry was heated to reflux and held at 117° to 119° C. for about 4 hours. The product was cooled to room temperature and added to 50 g of ice, diluted with 17 ml of chlorobenzene and neutralized to a pH of 8.0 with a 15% NaOH aqueous solution. The chlorobenzene solution was separated in a separatory funnel as the lower layer. The upper layer was diluted with 30 ml of water and extracted two times with 10 ml of chlorobenzene each. The combined chlorobenzene solutions were analyzed by GLC to indicate 2.9 g of compound (I) wherein X is chloro.

EXAMPLE 27

To 50 ml of toluene at 8° C. was added 10 g of phosgene under a nitrogen blanket. The solution was heated to 45° C. and a warm solution of 4 g of the compound of formula (VI) in 10 ml of dimethylformamide was added dropwise over 18 minutes with foaming and precipitation. The reaction mixture was stirred and heated to 56° C. over 2 hours. The product mixture was then cooled and mixed with 4 ml of water and neutralized with 20 ml of dilute NH$_4$OH (produced from 80 ml of concentrated NH$_4$OH diluted with water to 100 ml) and 2 g sodium carbonate to a pH of 8. Phase separation was made in a separatory funnel and the upper phase was vacuum stripped at 45° C. and a pressure of 65 mm of Hg to yield 1.9 g of the compound of formula (I) where X is Cl.

EXAMPLE 28

Step (c) to yield (XI) (X$^2$=Cl).

A solution of 0.5 g of the compound of formula (V) in 3 ml of toluene was treated gradually over 20 minutes at 25° to 40° C. with 0.55 ml of SO$_2$Cl$_2$ while stirring. The solution was then heated at 62° to 75° C. for 2 hours. The product was vacuum stripped over 1.75 hours at a bath temperature of 60° C. down to a pressure of 12 mm of Hg. The yield was 0.86 g of product. The product was extracted with 4 ml of warm toluene leaving 0.26 g of toluene-insoluble product. Of the insoluble product, 0.2 g was dissolved in a hot solvent mixture of 1 ml of acetone and 0.5 ml of cyclohexane which crystallized at room temperature. The yield of compound of formula (XI) was 0.11 g, mp 135° to 142° C. Characterization was made by MS and Elemental Analysis.

EXAMPLE 29

Step (c) to yield (XII) (X$^3$=Cl).

A solution of 0.5 g of the compound of formula (V) in 3 ml of chloroform was stirred and treated at 28° to 36° C. gradually with 0.55 ml of SO$_2$Cl$_2$. The solution was heated to 62° to 65° C. and precipitation of product occurred at that temperature. The solution was cooled to room temperature and filtered. The product was washed two times with 2 ml chloroform each. The yield was 0.26 g of product, mp 157° to 159° C. The chloroform washes where vacuum stripped to obtain 0.53 g of additional product. The product obtained was the hydrochloride salt of the compound of formula (XII) wherein X$^3$ is chloro as shown by MS, NMR and Elemental Analysis. After washing with hot acetone, the purified product had an mp of 160° to 162° C.

What is claimed is:

1. 5-Methyl-3,4-dihydro-2(1H)pyridone of the following formula (V):

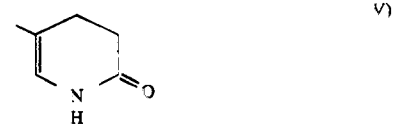

2. A method of preparing the dihydropyridone of the following formula (V):

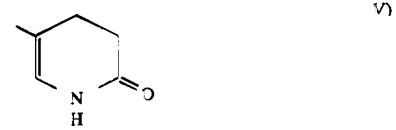

comprising the steps of:

(a) reacting propionaldehyde of the following formula (II) in a Michael addition with an acrylic compound of the following formula (III):

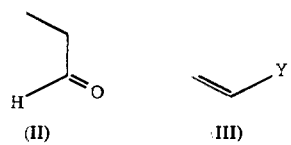

wherein Y is a moiety of the formula —COOR, —CONH$_2$ or —CN and R is alkyl of about 1 to 6 carbon atoms, aryl of about 6 to 10 carbon atoms, arylalkyl of about 1 to 8 carbon atoms in the alkyl portion and about 6 to 10 carbon atoms in the aryl portion which may be lower alkyl- or halo-substituted in the aryl or aryl portion, to produce an aldehyde of the following formula (IV):

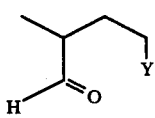 (IV)

and (b) cyclizing the aldehyde of formula (IV), adding an amine or ammonium salt when Y is COOR.

3. The method of claim 2, wherein step (a) is conducted in three stages which comprise:

(i) reacting propionaldehyde with a secondary amine of the formula $HNR^1R^2$, wherein $R^1$ and $R^2$ are lower alkyl groups of about 1 to 6 carbon atoms or $R^1$ and $R^2$ are joined together to form with the N atom a 5- or 6-membered heterocyclic ring, to form the enamine of the following formula (VII):

 (VII)

(ii) reacting the enamine of formula (VII) with the acrylic compound of formula (III) to form the compound of the following formula (VIII):

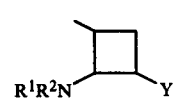 (VIII)

and (iii) hydrolyzing the compound of formula (VIII) to the aldehyde of formula (IV).

* * * * *